United States Patent [19]

Kaneko et al.

[11] Patent Number: 4,912,259
[45] Date of Patent: Mar. 27, 1990

[54] PENTADIENE AMINO COMPOUND

[75] Inventors: Kazuo Kaneko; Masahiko Yamaguchi; Michihiro Gonda; Kensaku Okano; Kazuyuki Wakasugi, all of Tokyo, Japan

[73] Assignee: Hodogaya Chemical Co., Ltd., Tokyo, Japan

[21] Appl. No.: 228,449

[22] Filed: Aug. 5, 1988

[51] Int. Cl.$^4$ .............................................. C07C 93/14
[52] U.S. Cl. .................................... 564/373; 564/374; 564/434; 564/442; 564/443
[58] Field of Search ............... 564/373, 374, 434, 442, 564/443

[56] References Cited

U.S. PATENT DOCUMENTS 3,954,887  5/1976  Wilke et al. ...................... 260/618 R
4,770,973  9/1988  Kanda et al. ..................... 430/151 X

FOREIGN PATENT DOCUMENTS 2121789  4/1984  United Kingdom .

OTHER PUBLICATIONS

Grif et al, Zh. Org. Khim, vol. 15 No. 12 (1979) pp. 2262-2267 (Eng. trans.).
Chemical Abstracts, vol. 92, No. 15, Apr. 14, 1980, p. 91, "Direction of Nucleophilic Addition to Polymethine Dyes", V. Kh. Grif, et al.

Primary Examiner—Richard L. Raymond
Attorney, Agent, or Firm—Oblon, Spivak, McClelland, Maier Neustadt

[57] ABSTRACT

A pentadiene compound of the formula:

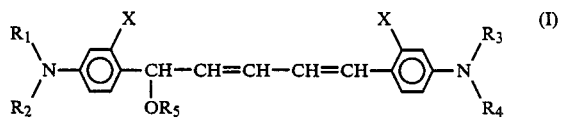

wherein each of $R_1$, $R_2$, $R_3$ and $R_4$ is a $C_1$-$C_4$ alkyl group or a substituted or unsubstituted aryl or aralkyl group, $R_5$ is an alkyl group, and X is a hydrogen atom, a $C_1$-$C_4$ alkyl group, a $C_1$-$C_4$ alkoxy group or a halogen atom.

6 Claims, No Drawings

PENTADIENE AMINO COMPOUND

The present invention relates to novel pentadiene compounds and recording materials wherein such compounds are used.

Heretofore, color formers have been employed in various recording materials. As typical examples, pressure sensitive recording materials, heat sensitive recording materials, electrical heat sensitive recording materials or photosensitive recording materials may be mentioned. The demand for such recording materials has rapidly increased with the development of information industry reflecting the present status of information age. Further, in recent years, computers have been employed widely for the rationalization of clerical works for office automation, or for the rationalization of various works for factory automation. For the input of information for such computers, optical character readers or optical bar code readers have been developed and have very much been used in recent years. Typical color formers which have commonly been used for recording materials such as pressure sensitive recording sheets, heat sensitive recording sheets or photosensitive recording sheets include phthalide compounds, fluoran compounds and triphenyl methane compounds. For example, as a typical phthalide compound, blue-emitting crystal violet lactone may be mentioned, as a typical fluoran compound, black-emitting 2-(2-chloroanylino)-6-dibutylaminofluoran may be mentioned, and as a typical triphenyl methane compound, blue-emitting leico crystal violet may be mentioned. However, these color formers exhibit no absorption in a near infrared region of from 700 to 1,000 nm. Therefore, recording images obtained by using such color formers are not suitable as recording images for optical character readers or optical bar code readers which have been widely used in recent years.

The present inventors have conducted extensive research to solve this problem and as a result, have found that pentadiene compounds having a certain specific structure are useful as color formers for recording materials. The present invention has been accomplished on the basis of this discovery.

The present invention provides a pentadiene compound of the formula:

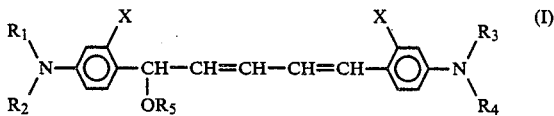

wherein each of $R_1$, $R_2$, $R_3$ and $R_4$ is a $C_1$–$C_4$ alkyl group or a substituted or unsubstituted aryl or aralkyl group, $R_5$ is an alkyl group, and X is a hydrogen atom, a $C_1$–$C_4$ alkyl group, a $C_1$–$C_4$ alkoxy group or a halogen atom.

The present invention also provides a recording material wherein a pentadiene compound of the formula I is used as a color former.

Now, the present invention will be described in detail with reference to the preferred embodiments.

The substituted or unsubstituted aryl or aralkyl group for each of $R_1$, $R_2$, $R_3$ and $R_4$ in the formula I is preferably a substituted or unsubstituted phenyl or benzyl group. The substitutents for the substituted aryl or aralkyl group include a $C_1$–$C_4$ alkyl group, a $C_1$–$C_4$ alkoxy group and a halogen atom. The alkyl group for $R_5$ is preferably a $C_1$–$C_8$ alkyl group. Likewise, the halogen atom for X is preferably a chlorine atom, a bromine atom or an iodine atom. Particularly preferred is a chlorine atom. X is preferably other than a hydrogen atom.

When brought in contact with a developing material such as an inorganic acid, an organic acid, a phenol compound or a derivative thereof, or a metal salt thereof, or an electron accepting substance such as an oxidizing agent (such as acid clay, zinc 3,5-di-t-butyl-salicylate, bis(3-chlorophenyl)thiourea, 4,4'-isopropylidenediphenol, zinc 4-nitorbenzoate or benzyl 4-hydroxybenzoate), the pentadiene compound of the present invention exhibits a color of bluish green or green and forms such a color clearly and with a high density.

Further, the recorded image obtained by a recording material wherein the compound of the present invention is used as a color former, such as a pressure sensitive recording sheet or a heat sensitive recording sheet, has a light absorbance also in a near infrared region of from 700 to 1,000 nm and is thus suitable for a recording material for an optical character reader or an optical bar code reader using as a light source a light of a near infrared region such as a semiconductor laser which has been widely used in recent years. The pentadiene compound of the formula I of the present invention can be prepared by a method which comprises reacting a bisstyrylcarbonium perchlorate derivative of the formula:

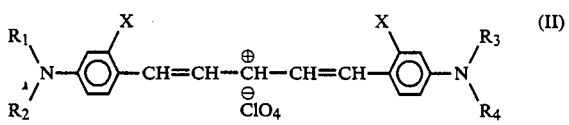

wherein $R_1$, $R_2$, $R_3$, $R_4$ and X are as defined above, with an alkali metal salt of an alcohol such as methanol of the formula:

wherein $R_5$ is as defined above, and M is an alkali metal at a temperature of from 20° to 100 C. in an alcohol solvent such as methanol.

The bisstyrylcarbonium perchlorate derivative of the formula II is a compound disclosed in, for example, Japanese Unexamined Patent Publication No. 231766/1985, and it can be synsesized by reacting the corresponding bisstyrylcarbinol derivative with a perchloric acid at a temperature of from 20° to 100° C. in an alcohol solvent such as methanol. Specific pentadiene compounds thus obtained are as follows:

(1) 1,5-bis[4-(N,N-dimethylamino)phenyl]-5-methoxypenta-1,3-diene
(2) 1,5-bis[4-(N,N-diethylamino)phenyl]-5-methoxypenta-1,3-diene
(3) 1,5-bis[4-(N,N-di-n-butylamino)phenyl]-5-methoxypenta-1,3-diene
(4) 1,5-bis[4-(N,N-di-n-propylamino)phenyl]-5-methoxypenta-1,3-diene
(5) 1,5-bis[4-(N,N-dimethylamino)phenyl]-5-ethoxypenta-1,3-diene
(6) 1,5-bis[4-(N,N-diethylamino)phenyl]-5-ethoxypenta-1,3-diene
(7) 1,5-bis[4-(N-methyl-N-ethylamino)phenyl]-5-methoxypenta-1,3-diene (8) 1,5-bis[4-(N-methyl-N-ethylamino)phenyl]-5-ethoxypenta-1,3-diene
(9) 1,5-bis[4-(N,N-dimethylamino)phenyl]-5-propoxypenta-1,3-diene
(10) 1,5-bis[3-(N,N-dimethylamino)phenyl]-5-butoxypenta-1,3-diene
(11) 1,5-bis[4-(N,N-dimethylamino)-2-methyl-phenyl]-5-methoxypenta-1,3-diene
(12) 1,5-bis[4-(N,N-diethylamino)-2-methyl-phenyl]-5-methoxypenta-1,3-diene
(13) 1,5-bis[4-(N,N-di-n-butylamino)-2-methyl-phenyl]-5-methoxypenta-1,3-diene
(14) 1,5-bis[4-(N,N-di-n-propylamino)-2-chloro-phenyl]-5-methoxypenta-1,3-diene
(15) 1,5-bis[4-(N,N-dimethylamino)-2-methyl-phenyl]-5-ethoxypenta-1,3-diene
(16) 1,5-bis[4-(N,N-diethylamino-2-ethoxy-phenyl]-5-methoxypenta-1,3-diene
(17) 1,5-bis[4-(N-methyl-N-ethylamino-2-methoxy-phenyl]-5-methoxypenta-1,3-diene
(18) 1,5-bis[4-(N-methyl-N-phenylamino)-2-methyl-phenyl]-5-methoxypenta-1,3-diene
(19) 1,5-bis[4-(N-methyl-N-benzylamino)-2-methyl-phenyl]-5-methoxypenta-1,3-diene
(20) 1,5-bis[4-(N-methyl-N-ethylamino)-2-propyl-phenyl]-5-ethoxypenta-1,3-diene
(21) 1,5-bis[4-(N,N-dimethylamino)-2-bromo-phenyl]-5-propoxypenta-1,3-diene
(22) 1,5-bis[4-(N,N-dimethylamino)-2-chloro-phenyl]-5-butoxypenta-1,3-diene Among the pentadiene compounds, those of the formula I wherein X is other than a hydrogen atom are particularly superior in the stability to lights.

Now, the present invention will be described in further detail with reference to Examples. However, it should be understood that the present invention is by no means restricted to such specific Examples. In the following description, "parts" and "%" mean "parts by weight" and "% by weight".

EXAMPLE 1

10.0 parts of 4-(N,N-dimethylamino)benzaldehyde, 1.95 parts of acetone and 13.4 parts of a 10% sodium hydroxide aqueous solution were dissolved in 70 ml of ethanol and reacted for 8 hours under stirring at a temperature of from 40° to 50° C. Precipitated crystals were collected by filtration and washed with 30 ml of ethanol and then with 60 ml of water and dried to obtain 20.0 parts of orange yellow crystals. This product was identified to be bis[4-(N,N-dimethylamino)stryl]ketone, since it had a melting point of from 189.0° to 191.0° C. and showed absorption peaks of substituted ethylenic carbon at 120.5 ppm and 142.2 ppm and an absorption peak of carbonyl carbon at 187.9 ppm by the $^{13}$CNMR analysis. Then, 10 parts of this ketone was dissolved in a solvent mixture comprising 100 parts of tetrahydrofulfuryl alcohol and 150 parts of THF (tetrahydrofuran), and 3.6 parts of sodium boron hydride was added thereto. The mixture was reacted at a temperature of from 30° to 50° C. This reaction solution was poured into 1,500 ml of water, and precipitated crystals were separated by filtration, washed with water and dried to obtain 9.0 parts of slightly yellow crystals. This product was identified to be bis[4-(N,N-dimethylamino)styryl]carbinol, since it had a melting point of from 80° to 90° C. and showed absorption peaks of substituted ethylenic carbon at 126.6 ppm and 130.5 ppm and an absorption peak of carbinol carbon at 74.3 ppm by the $^{13}$CNMR analysis. Then, 5.0 parts of this carbinol was dissolved in 50 parts of THF, and a solution mixture comprising 2.6 parts of 60% perchloric acid and 30 parts of glacial acetic acid was added at room temperature, and precipitated crystals were collected by filtration, washed with water and dried to obtain 5.5 parts of blackish green crystals. This product was identified to be bis[4-(N,N-dimethylamino)styryl]carbonium perchlorate of the formula II. Then, 5.0 parts of this carbonium perchlorate was dispersed in 50 parts of methanol, and 2.4 parts of a 28% sodium methoxide methanol solution was added thereto. The mixture was reacted under reflux for 1 hour and then cooled, whereupon precipitated crystals were collected by filtration, washed with water and dried to obtain 2.9 parts of slightly yellow crystals. This product was identified to be 1,5-bis[4-(N,N-dimethylamino)phenyl]-5-methoxypenta-1,3-diene, since it had a melting point of from 91.0° to 92.5° C. and showed an absorption peak of quaternary carbon at 83.9 ppm, four absorption peaks of vinyl carbon at 124.3 ppm, 132.0 ppm, 132.2 ppm and 132.8 ppm and absorption peaks of a methyl group substituted to a nitrogen atom at 40.4 ppm and 40.6 ppm. This product was dissolved in 95% acetic acid, and the light absorption characteristics were measured, whereby the maximum absorption characteristics were measured, whereby the maximum absorption was found at 800 nm. Further, when developed by bisphenol A as a typical electron accepting developer, it showed the maximum absorption at 830 nm.

EXAMPLE 2

40.8 parts of 4-(N,N-dimethylamino)-2-methyl-benzaldehyde, 7.3 parts of acetone and 45.0 parts of 10% sodium hydroxide were dissolved in 350 ml of ethanol and reacted for 30 hours under stirring at a temperature of from 20° to 50° C. Precipitated crystals were collected by filtration, washed with 120 ml of ethanol and then with 120 ml of water and dried to obtain 35.0 parts of orange yellow crystals. This product had a melting point of from 181.0° to 181.5° C. From the analysis by the $^{13}$CNMR and the elemental analysis, this product was identified to be bis[4-(N,N-dimethylamino)-2-methyl-styryl]ketone. 24.4 parts of this ketone was dissolved in 490 ml of tetrahydrofuran, and 175 ml of methanol and 70 ml of water were added thereto. The mixture was maintained at 15° C., and 2.65 parts of sodium boron hydride was added thereto. The mixture was stirred for 24 hours at a temperature of from 15° to 25° C. Precipitated crystals were removed by filtration, and the filtrate was maintained at a temperature of from 10° to 15° C., and a mixture comprising 14.7 parts of 60% perchloric acid and 190 parts of acetic acid was dropwise added thereto over a period of 30 minutes. The mixture was stirred for further 30 minutes. Precipitated crystals were collected by filtration, washed with 200 ml of tetrahydrofuran and with 100 ml of water and dried to obtain 19.6 parts of blackish green crystals. This product gradually decomposed at a temperature of 206° C. or higher. Further, this product was identified to be bis[4-N,N-dimethylamino)-2-methyl-styryl]carbonium perchlorate of the formula II, since it showed absorption peaks of substituted ethylenic carbon at 125.4 ppm and 151.5 ppm and an absorption peak of a central carbon at 159.7 ppm as the result of the analysis by the $^{13}$CNMR. Then, 16.6 parts of this carbonium perchlorate was dispersed in 120 parts of anhydrous methanol, and 7.4 parts of a 28% sodium methoxide methanol solution was added. The mixture was reacted at 50° C. for 30 minutes and under reflux for 30 minutes, and then cooled. Precipitated crystals were collected by filtration, washed with water and dried to obtain 11.7 parts of slightly yellow crystals. This product was identified to be 1,5-bis[4-(N,N-dimethylamino) -2-methyl-phenyl]-5-methoxypenta-1,3-diene, since it had a melting point of from 110.8° to 112.2° C. and showed an absorption peak of methoxy-substituted $SP^3$ carbon at 81.2 ppm, four absorption peaks of vinyl carbon at 127.7 ppm, 130.2 ppm, 131.5 ppm and 132.5 ppm, absorption peaks of a methyl group substituted on nitrogen at 40.5 ppm and 40.6 ppm and absorption peaks of a methyl group substituted on a benzene carbon at 19.9 ppm and 20.5 ppm, as the results of the analysis by the $^{13}CNMR$. Further, this product was dissolved in 95% acetic acid and the light absorbing characteristics were measured, whereby it showed the maximum absorption ($\lambda_{max}$) at 800 nm, and the molar absorbance coefficient ($\epsilon$) was $1.47 \times 10^5$.

EXAMPLE 3

In the same manner as in Example 2, 1,5-bis[4-(N,N-diethylamino)-2-methyl-phenyl]-5-methoxypenta-1,3-diene was prepared. This product was dissolved in 95% acetic acid, and the light absorption characteristics were measured, whereby it showed the maximum absorption ($\lambda_{max}$) at 805 nm.

EXAMPLE 4

In the same manner as in Example 2, 1,5-bis[4-(N,N-diethylamino)-2-chloro-phenyl]-5-methoxypenta-1,3-diene was prepared. This product was dissolved in 95% acetic acid, and the light absorption characteristics were measured, whereby it showed the maximum absorption ($\lambda_{max}$) at 807 nm.

EXAMPLE 5

In the same manner as in Example 2, 1,5-bis[4-(N,N-diethylamino)-2-ethoxy-phenyl]-5-methoxypenta-1,3-diene was prepared. This product was dissolved in 95% acetic acid, and the light absorption characteristics were meareud, whereby it showed the maximum absorption ($\lambda_{max}$) at 805 nm.

EXAMPLE 6

14 parts of gelatin having an isoelectric point of 8.5 and 12 parts of gum arabic were dissolved in 150 parts of deionized water at 50° C., and 3.5 parts of 10% Turkey red oil was added as an emulsifier thereto. Then, 70 parts of Hysol SAS-296 (diallylethane type oil, manufactured by Nippon Sekiyu Kagaku K.K.) containing 3% of 1,5-bis[4-(N,N-dimethylamino)-2-methyl-phenyl]-5-methoxypenta-1,3-diene was added thereto, and the mixture was emulsified by a honomixer under a condition of 7,000 rpm to obtain an O/W emulsion. To this emulsion, 100 parts of deionized water of 40° C. was added, and a 10% acetic acid aqueous solution was dropwise added under stirring by a mixer with a stirring-type stirrer at 350 rpm to adjust the pH to 4.3.

Then, 13 parts of an aqueous solution containing 20% of Melment F10 (Sodium salt of sulfonated melamine resin, manufactured by Showa Denko K.K.) and 3.5 parts of an aqueous solution containing 40% of Newcol 271A (Disodium dodecyl diphenylether disulfonate, manufactured by Japan Emulsifier Co., Ltd.) were added thereto, and the mixture was cooled from the outside of the container while continuing the stirring to bring the temperature of the solution to 8° C. Then, 5.5 parts of a 37% formalin solution was added thereto, and a 10% sodium hydroxide aqueous solution was dropwise added over a period of 15 minutes to adjust the pH to 9.5. While continuing the stirring, the solution temperature was brought to 50° C. over a period of 30 minutes to obtain a microcapsule slurry of 1,5-bis[4-(N,N-dimethylamino)-2-methyl-phenyl]-5-methoxypenta-1,3-diene-dissolved oil.

This microcapsule slurry was coated on a paper sheet and dried and then brought in contact with a commercially available pressure sensitive developer sheet, whereupon a tensile pressure or a typewriter impact was applied, whereby a developed recording image of greenish blue was obtained.

EXAMPLE 7

2.0 parts of 1,5-bis[4-(N,N-dimethylamino)-2-methyl-phenyl]-5-methoxypenta-1,3-diene and 20 parts of a 10% polyvinyl alcohol aqueous solution were dispersed and mixed by a ball mill at room temperature for 24 hours to obtain a colorless slurry which is designated as solution A. The particle size of the solid substance in this slurry was about 3 $\mu$m.

On the other hand, 7.5 parts of bisphenol A was dispersed together with 40 parts of a 10% polyvinyl alcohol aqueous solution and 10 parts of deionized water by a ball mill at room temperature for 24 hours to obtain a slurry which is desingnated as solution B. The particle size of the solid substance in this slurry was about 5 $\mu$m.

Solutions A and B were combined and mixed at room temperature over a period of 1 hour and uniformly dispersed and mixed to obtain a mixed slurry. This mixed slurry was coated by a wire bar coater on one side of an ordinary paper of 50 g/m² to have a uniform coating thickness and air-dried at room temperature to obtain a heat sensitive recording sheet having a substantially colorless heat sensitive layer.

Heat sensitive recording sheets prepared as described above, were subjected to color development by using a heat inclination tester, whereby in each case, a developed color recording image of bluish green was obtained.

EXAMPLE 8

2.0 parts of 1,5-bis[4-(N,N-dimethylamino)phenyl]-5-methoxypenta-1,3-diene and 20 parts of a 10% polyvinyl alcohol aqueous solution were dispersed and mixed in a ball mill at room temperature for 24 hours to obtain a colorless slurry which is designated as solution C. The particle size of the solid substance in this slurry was about 3 $\mu$m.

On the other hand, 7.5 parts of bisphenol A was dispersed together with 40 parts of a 10% polyvinyl alcohol aqueous solution and 10 parts of deionized water by a ball mill at room temperature for 24 hours to obtain a slurry which is designated as solution D. The particle size of the solid substance in this slurry was about 5 $\mu$m.

Solutions C and D were combined and mixed at room temperature over a period of 1 hour and uniformly dispersed and mixed to obtain a mixed slurry. This mixed slurry was coated by means of a wire bar coater on one side of a normal paper of 50 g/m² to have a uniform coating thickness and air-dried at room temperature to obtain a heat sensitive recording sheet having a substantially colorless heat sensitive layer.

The heat sensitive recording sheets prepared as described above were subjected to color development by using a heat inclination tester, whereby in each case, a developed-color recording image of bluish green was obtained.

As described in the foregoing, the present invention provides a novel color former which has a strong absorption in a near infrared region under a color-developed state, which is excellent in the solubility in capsule oil when used for a pressure sensitive recording sheet and which has excellent sensitivity characteristics when used for a heat sensitive recording sheet, since it has a low melting point.

We claim:

1. A pentadiene compound of the formula:

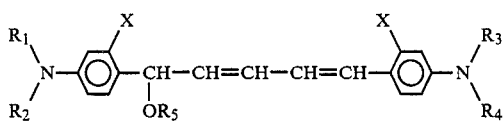

wherein each of $R_1$, $R_2$, $R_3$ and $R_4$ is a $C_1$-$C_4$ alkyl group, a substituted or unsubstituted aryl or aralkyl group where said substituents are selected from the group consisting of $C_1$-$C_4$ alkyl, $C_1$-$C_4$ alkoxy and halogen; $R_5$ is an alkyl group and X is a $C_1$-$C_4$ alkyl group, a $C_1$-$C_4$ alkoxy group or a halogen atom.

2. The pentadiene compound according to claim 1, wherein the aryl or aralkyl group for each of $R_1$, $R_2$, $R_3$, and $R_4$ is a substituted or unsubstituted phenyl or benzyl group, where said substitutents are selected from the group consisting of $C_1$-$C_4$ alkyl, $C_1$-$C_4$ alkoxy and halogen.

3. The pentadiene compound according to claim 1, wherein the alkyl group for $R_5$ is a $C_1$-$C_8$ alkyl group.

4. The pentadiene compound to claim 1, wherein the halogen atom for X is a chlorine atom, a bromine atom or an iodine atom.

5. The pentadiene compound to claim 1, where X is a chlorine atom.

6. The pentadiene compound of claim 1, wherein X is methyl.

* * * * *